(12) United States Patent
Ota et al.

(10) Patent No.: US 10,513,491 B2
(45) Date of Patent: Dec. 24, 2019

(54) SULFONIC ACID ESTER COMPOUND AND USE THEREFOR

(71) Applicant: NISSAN CHEMICAL CORPORATION, Tokyo (JP)

(72) Inventors: Hirofumi Ota, Funabashi (JP); Toshiyuki Endo, Funabashi (JP)

(73) Assignee: NISSAN CHEMICAL CORPORATION, Tokyo (JP)

( * ) Notice: Subject to any disclaimer, the term of this patent is extended or adjusted under 35 U.S.C. 154(b) by 0 days.

(21) Appl. No.: 16/309,845

(22) PCT Filed: Jun. 14, 2017

(86) PCT No.: PCT/JP2017/021976
§ 371 (c)(1),
(2) Date: Dec. 13, 2018

(87) PCT Pub. No.: WO2017/217457
PCT Pub. Date: Dec. 21, 2017

(65) Prior Publication Data
US 2019/0169120 A1    Jun. 6, 2019

(30) Foreign Application Priority Data

Jun. 16, 2016 (JP) ................. 2016-119818

(51) Int. Cl.
*C07C 309/75* (2006.01)
*H01L 51/50* (2006.01)
*H01L 51/00* (2006.01)

(52) U.S. Cl.
CPC ........ *C07C 309/75* (2013.01); *H01L 51/5072* (2013.01); *H01L 51/0051* (2013.01)

(58) Field of Classification Search
None
See application file for complete search history.

(56) References Cited

U.S. PATENT DOCUMENTS

| 4,143,023 | A | 3/1979 | Mark et al. |
| 2006/0115652 | A1 | 6/2006 | Yoshimoto et al. |
| 2007/0043222 | A1 | 2/2007 | Yoshimoto et al. |
| 2007/0105030 | A1 | 5/2007 | Yoshimoto et al. |
| 2017/0104161 | A1 | 4/2017 | Otani |

FOREIGN PATENT DOCUMENTS

| JP | 54-16562 A | 2/1979 |
| JP | 7-134416 A | 5/1995 |
| JP | 2002-151272 A | 5/2002 |
| JP | 5136795 B2 | 2/2013 |
| JP | 2015-213147 A | 11/2015 |
| WO | WO 2004/043117 A1 | 5/2004 |
| WO | WO 2005/000832 A1 | 1/2005 |
| WO | WO 2005/043962 A1 | 5/2005 |
| WO | WO 2007/099808 A1 | 9/2007 |
| WO | WO 2015/186688 A1 | 12/2015 |

OTHER PUBLICATIONS

"Chemical Reactions Exhibiting Proliferation of Catalytic Molecules", Kino Zairyo, 2004, vol. 24, pp. 72-82.
International Search Report for PCT/JP2017/021976 dated Sep. 5, 2017.
Nenitzescu et al., "Über Die Alkylierung Des Aromatischen Kerns MIT Sulfonsäureestern", Chemische Berichte, 1957, vol. 90, pp. 585-592.
Written Opinion of the International Searching Authority for PCT/JP2017/021976 (PCT/ISA/237) dated Sep. 5, 2017.

*Primary Examiner* — Samantha L Shterengarts
(74) *Attorney, Agent, or Firm* — Birch, Stewart, Kolasch & Birch, LLP

(57) ABSTRACT

Provided is a sulfonic acid ester compound represented by formula (1).

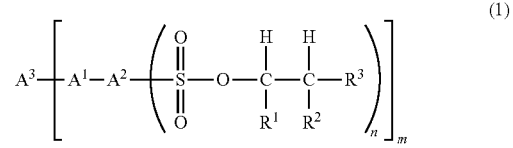

(In the formula, $R^1$ and $R^2$ each independently represent a hydrogen atom, or a straight-chain or branched monovalent aliphatic hydrocarbon group. $R^3$ represents a straight-chain or branched monovalent aliphatic hydrocarbon group. The sum of the carbon numbers of $R^1$, $R^2$ and $R^3$ is 6 or greater. $A^1$ represents —O— or —S—. $A^2$ represents an aromatic group having a valence of (n+1). $A^3$ represents a hydrocarbon group which has a valence of m, and is unsubstituted or has a substituent that contains one or more aromatic rings. m represents an integer satisfying $2 \leq m \leq 4$. n represents an integer satisfying $1 \leq n \leq 4$).

13 Claims, No Drawings

SULFONIC ACID ESTER COMPOUND AND USE THEREFOR

TECHNICAL FIELD

The present invention relates to a sulfonic acid ester compound and uses therefor.

BACKGROUND ART

Charge-transporting thin films made of organic compounds are used as light-emitting layers and charge-injecting layers in organic electroluminescent (EL) devices. In particular, a hole-injecting layer is responsible for transferring charge between an anode and a hole-transporting layer or a light-emitting layer, and thus carries out an important function for achieving low-voltage driving and high brightness in organic EL devices.

In the past few years, charge-transporting varnishes composed of a uniform solution of a low-molecular-weight oligoaniline-based material or an oligothiophene-based material dissolved in an organic solvent have been discovered and it has been reported that, by inserting a hole-injecting layer obtained from such a varnish in an organic EL device, an underlying substrate leveling effect and excellent organic EL device properties can be obtained (Patent Documents 1 to 3). Moreover, it has also been reported that, by using a 1,4-benzodioxanesulfonic acid compound as an electron-accepting substance (Patent Document 4), the driving voltage of organic EL devices can be lowered.

Yet, because sulfonic acid compounds generally have a low solubility in organic solvents, there tend to be limitations on the solvent used when preparing an organic solution; that is, it has been necessary to use a high proportion of a highly polar organic solvent which has a high solvating power, such as N,N-dimethylacetamide or N-methylpyrrolidone. Organic solutions containing a high proportion of a highly polar organic solvent sometimes cause damage to parts of inkjet coating devices or to organic structures such as insulating films and barrier membranes formed on substrates. Moreover, because sulfonic acid compounds are highly polar, purification by silica gel column chromatography, liquid/liquid extraction, and salt removal by an operation such as water rinsing are difficult.

At the same time, sulfonic acid ester compounds are known to be materials which have a high solubility in various organic solvents and which generate strong organic acids under external stimulation such as heating or chemical action. The cyclohexyl ester of sulfonic acid has been reported as a specific example of a compound which generates sulfonic acid under heating (Non-Patent Document 1). Notice has also been taken of this sulfonic acid ester compound in terms of the concept of a thermal acid generator (Patent Document 5, Non-Patent Document 2). Yet, particularly with regard to sulfonic acid ester compounds substituted on the electron-deficient aromatic ring of an aromatic disulfonic acid or the like, there has existed a desire for the creation of highly stable sulfonic acid ester compounds that readily decompose under slight heating or via reaction with water, a basic substance or the like.

PRIOR ART DOCUMENTS

Patent Documents

Patent Document 1: JP-A 2002-151272
Patent Document 2: WO 2004/043117
Patent Document 3: WO 2005/043962
Patent Document 4: WO 2005/000832
Patent Document 5: JP-A H07-134416
Patent Document 6: JP No. 5136795

Non-Patent Documents

Non-Patent Document 1: *Chemische Berichte*, 90, pp. 585-592 (1957)
Non-Patent Document 2: *Kino Zairyo*, 24, pp. 72-82 (2004)

SUMMARY OF INVENTION

Technical Problem

The inventors, in order to resolve the above problems, have reported sulfonic acid ester compounds that possess a high stability and also have a high solubility in a wide range of organic solvents (Patent Document 6). However, although these sulfonic acid ester compounds have a better stability and a better solubility in organic solvents than the sulfonic acid compounds and sulfonic acid ester compounds that have hitherto been used, dissolving them in low-polarity solvents requires a high temperature and prolonged stirring. Moreover, when such compounds are formed into a solution, settling occurs with long-term storage. Hence, there has remained room for improvement, both in the solubility of these compounds in organic solvents and in their stability.

It is therefore an object of the invention to provide sulfonic acid ester compounds which have an excellent solubility in low-polarity solvents, which have an excellent stability as varnishes, and which, when employed in organic EL devices, make it possible to achieve excellent device characteristics.

Solution to Problem

The inventors have conducted extensive investigations in order to achieve the above object. As a result, they have discovered that esters of specific sulfonic acid compounds and fatty alcohol compounds have an excellent solubility in low-polarity solvents compared with conventional sulfonic acid ester compounds, and moreover, when rendered into solutions, also have an excellent shelf stability.

Accordingly, the invention provides the following sulfonic acid ester compound and uses therefor.

1. A sulfonic acid ester compound of formula (1) below

[Chem. 1]

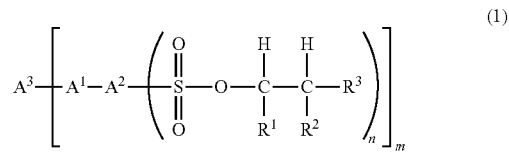

wherein $R^1$ and $R^2$ are each independently a hydrogen atom or a linear or branched monovalent aliphatic hydrocarbon group, and $R^3$ is a linear or branched monovalent aliphatic hydrocarbon group, the total number of carbon atoms on $R^1$, $R^2$ and $R^3$ being 6 or more;
$A^1$ represents —O— or —S—, $A^2$ is an aromatic group having a valence of n+1, and $A^3$ is a substituted or unsubstituted m-valent hydrocarbon group containing one or more aromatic ring; and m is an integer that satisfies the condition 2≤m≤4, and n is an integer that satisfies the condition 1≤n≤4.

2. The sulfonic acid ester compound of 1 above, wherein $R^1$ is a hydrogen atom, and $R^2$ and $R^3$ are each independently an alkyl group of 1 to 6 carbon atoms.

3. The sulfonic acid ester compound of 1 or 2 above, wherein $A^2$ is a group derived from naphthalene or anthracene.

4. The sulfonic acid ester compound of 3 above, wherein $A^2$ is a group derived from naphthalene.

5. The sulfonic acid ester compound of any of 1 to 4 above, wherein $A^3$ is a group derived from perfluorobiphenyl.

6. The sulfonic acid ester compound of any of 1 to 5 above, wherein m is 2.

7. The sulfonic acid ester compound of any of 1 to 6 above, wherein n is 2.

8. An electron-accepting substance precursor comprising the sulfonic acid ester compound of any of 1 to 7 above.

9. A charge-transporting varnish which includes the electron-accepting substance precursor of 8 above, a charge-transporting substance and an organic solvent.

10. The charge-transporting varnish of 9 above, wherein the organic solvent is a low-polarity organic solvent.

11. The charge-transporting varnish of 9 or 10 above, wherein the charge-transporting substance is an aniline derivative.

12. A charge-transporting thin film produced using the charge-transporting varnish of any of 9 to 11 above.

13. An organic EL device which includes the charge-transporting thin film of 12 above.

Advantageous Effects of Invention

The sulfonic acid ester compound of the invention has a high solubility in a broad range of organic solvents, including low-polarity solvents. Therefore, a charge-transporting varnish can be prepared from this compound even when a low-polarity solvent is used or the proportion of high-polarity solvent is decreased. Moreover, when the compound is rendered into a solution, the shelf stability of the solution is also excellent. Not only can low-polarity organic solvent-based charge-transporting varnishes be applied with inkjet coaters, which have a poor solvent resistance, they can be used even in cases where a structure having a poor solvent resistance, such as an insulating film or a barrier membrane, is present on a substrate. As a result, amorphous solid thin-films having a high flatness can be produced without difficulty.

Also, because thin films obtained from the charge-transporting varnish of the invention have a high charge transportability, when such a film is used as a hole-injecting layer or a hole-transporting layer, the driving voltage of the organic EL device can be lowered. By taking advantage of the high flatness and high charge transportability of these thin films, it is also possible to employ the thin films as hole-transporting layers in solar cells, as fuel cell electrodes, as protective films for capacitor electrodes, and as antistatic films.

DESCRIPTION OF EMBODIMENTS

[Sulfonic Acid Ester Compound]

The sulfonic acid ester compound of the invention is represented by formula (1) below.

[Chem. 2]

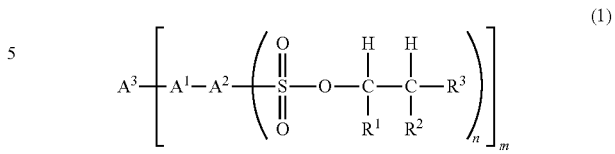

In formula (1), $R^1$ and $R^2$ are each independently a hydrogen atom or a linear or branched monovalent aliphatic hydrocarbon group, and $R^3$ is a linear or branched monovalent aliphatic hydrocarbon group. The total number of carbon atoms on $R^1$, $R^2$ and $R^3$ is 6 or more. There is no upper limit in the total number of carbon atoms on $R^1$, $R^2$ and $R^3$, although the total number of carbon atoms is preferably not more than 20, and more preferably not more than 10.

Examples of the linear or branched monovalent aliphatic hydrocarbon group include, without particular limitation, alkyl groups of 1 to 18 carbon atoms such as methyl, ethyl, n-propyl, isopropyl, n-butyl, isobutyl, tert-butyl, n-hexyl, n-octyl, 2-ethylhexyl and decyl groups; and alkenyl groups of 2 to 18 carbon atoms such as vinyl, 1-propenyl, 2-propenyl, isopropenyl, 1-methyl-2-propenyl, 1-butenyl, 2-butenyl, 3-butenyl and hexyl groups.

$R^1$ is preferably a hydrogen atom, and $R^2$ and $R^3$ are preferably alkyl groups of 1 to 6 carbon atoms. In this case, $R^2$ and $R^3$ may be the same or different.

In formula (1), $A^1$ represents —O— or —S—, and is preferably —O—. $A^2$ is an aromatic group having a valence of n+1. $A^3$ is a substituted or unsubstituted m-valent hydrocarbon group containing one or more aromatic ring.

The (n+1)-valent aromatic group represented by $A^2$ is a group obtained by removing n+1 hydrogen atoms from the aromatic ring on an aromatic compound. Examples of the aromatic compound include benzene, toluene, xylene, naphthalene, anthracene and phenanthrene. Of these, $A^2$ is preferably a group derived from naphthalene or anthracene, and more preferably a group derived from naphthalene.

The substituted or unsubstituted m-valent hydrocarbon group that contains one or more aromatic ring and is represented by $A^3$ is a group obtained by removing m atoms or atomic groups bonded to the carbon skeleton from a substituted or unsubstituted hydrocarbon containing one or more aromatic ring. Examples of the hydrocarbon include benzene, toluene, xylene, ethylbenzene, biphenyl, naphthalene, anthracene and phenanthrene in which some or all hydrogen atoms on these groups are substituted with, for example, hydroxyl groups, amino groups, silanol groups, thiol groups, carboxyl groups, sulfonic acid ester groups, phosphoric acid groups, phosphoric acid ester groups, ester groups, thioester groups, amide groups, nitro groups, monovalent hydrocarbon groups, organooxy groups, organoamino groups, organosilyl groups, organothio groups, acyl groups, sulfone groups and halogen atoms.

From the standpoint of trying to enhance the durability and charge transportability of the sulfonic acid ester compound of formula (1), $A^3$ is preferably a divalent or trivalent group derived from 1,3,5-triazine, a divalent or trivalent group derived from substituted or unsubstituted benzene, a divalent or trivalent group derived from substituted or unsubstituted toluene, a divalent group derived from substituted or unsubstituted p-xylene, a divalent or trivalent group derived from substituted or unsubstituted naphthalene, or a divalent to tetravalent group derived from perfluorobiphenyl; and more preferably a divalent perfluorobiphenyl group.

In formula (1), the subscript m is an integer that satisfies the condition 2≤m≤4, with 2 being preferred. The subscript n is an integer that satisfies the condition 1≤n≤4, with 2 being preferred.

The sulfonic acid ester compound of the invention can be synthesized by, for example, as shown in the reaction scheme below, reacting a sulfonic acid salt compound of formula (1″) with a halogenating agent so as to synthesize a sulfonyl halide compound of formula (1′) below (referred to below as "Step 1"), and then reacting this sulfonyl halide compound with an alcohol compound of formula (2) (referred to below as "Step 2").

[Chem. 3]

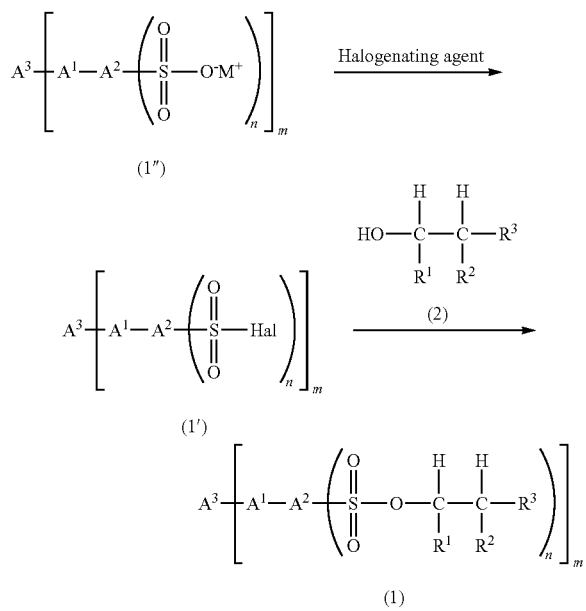

Here, $A^1$ to $A^3$, $R^1$ to $R^3$, m and n are as defined above; $M^+$ is a monovalent cation such as a sodium ion, potassium ion, pyridinium ion or quaternary ammonium ion; and Hal is a halogen atom such as a chlorine atom or bromine atom.

The sulfonic acid salt compound of formula (1″) can be synthesized by a known method.

Examples of the halogenating agent used in Step 1 include thionyl chloride, oxalyl chloride, phosphorus oxychloride and phosphorus(V) chloride; thionyl chloride is preferred. The amount of halogenating agent used is not limited, so long as it is at least one mole per mole of the sulfonic acid salt compound, although use in an amount that, expressed as a weight ratio, is from 2 to 10 times the amount of the sulfonic acid salt compound is preferred.

The reaction solvent used in Step 1 is preferably a solvent that does not react with the halogenating agent, examples of which include chloroform, dichloroethane, carbon tetrachloride, hexane and heptane, although the absence of a solvent is preferred. When the reaction is carried out in the absence of a solvent, the halogenating agent is preferably used in at least the amount at which the system becomes a uniform solution at the time of reaction completion. The reaction temperature may be set to from about 0° C. to about 150° C., although the reaction temperature is preferably from 20 to 100° C. and at or below the boiling point of the halogenating agent used. Following reaction completion, the crude product obtained by vacuum concentration or the like is generally used in the next step.

The alcohol compound of formula (2) is preferably 2-ethyl-1-hexanol, 2-butyl-1-octanol, 1-octanol or 3-nonanol, and more preferably 2-ethyl-1-hexanol, 2-butyl-1-octanol or 1-octanol.

In Step 2, a base may be concomitantly used. Examples of bases that may be used include sodium hydride, pyridine, triethylamine and diisopropylethylamine. Sodium hydride, pyridine and triethylamine are preferred. The base is preferably used in an amount that ranges from one mole per mole of the sulfonyl halide compound (1′) up to the amount of solvent.

Various organic solvents may be used as the reaction solvent in Step 2, although tetrahydrofuran, dichloroethane, chloroform and pyridine are preferred. The reaction temperature, although not particularly limited, is preferably from 0 to 80° C. Following reaction completion, pure sulfonic acid ester compound can be obtained by work-up and purification using customary methods such as vacuum concentration, liquid/liquid extraction, water rinsing, reprecipitation, recrystallization and chromatography. The pure sulfonic acid ester compound thus obtained can be rendered into a high-purity sulfonic acid compound by being subjected to heat treatment or the like.

[Electron-Accepting Substance Precursor]

The sulfonic acid ester compound of formula (1), given that sulfonic acid forms with heat treatment or the like and that this sulfonic acid compound exhibits electron-accepting properties, can be advantageously used as an acid generator or as an electron-accepting substance precursor. Here, the electron-accepting substance is a substance which may be used to increase the electron transportability and the uniformity of film formation, and is synonymous with an electron-accepting dopant.

Because the sulfonic acid ester compound of formula (1) exhibits a high solubility in a broad range of solvents, including low-polarity solvents, the physical properties of the solution can be adjusted using a variety of solvents, and the solution has a high coatability. Therefore, it is preferable for coating to be carried out while the solution is in the state of a sulfonic acid ester, and for sulfonic acid to be generated when the applied film is dried or baked. Because it is desirable for the sulfonic acid ester to be stable at room temperature and at or below the baking temperature, the temperature at which sulfonic acid is generated from the sulfonic acid ester is typically from 40 to 260° C. Taking into account the high stability of the sulfonic acid ester within the varnish and the ease of dissociation during baking, the temperature is preferably from 80 to 230° C., and more preferably from 120 to 180° C.

The sulfonic acid ester compound of formula (1) can be rendered into a charge-transporting varnish by dissolution or dispersion, together with the charge-transporting substance serving as the central part of the charge transport mechanism, in an organic solvent.

[Charge-Transporting Varnish]

The charge-transporting varnish of the invention includes an electron-accepting substance precursor consisting of the compound of formula (1), a charge-transporting substance, and an organic solvent. In this invention, "charge-transportability" is synonymous with electrical conductivity. Also, "charge-transporting varnish" may refer to a varnish which itself has charge transportability or to one from which there can be obtained a solid film having charge transportability.

[Charge-Transporting Substance]

A charge-transporting substance hitherto used in the organic EL field may be used as the above charge-transporting substance. Examples include charge-transporting oligomers such as aniline derivatives, thiophene derivatives and pyrrole derivatives. The molecular weight of the charge-transporting oligomer is typically from 200 to 8,000. From the standpoint of preparing a varnish which gives thin films having a high charge transportability, the molecular weight is preferably at least 300, more preferably at least 400, and even more preferably at least 500. From the standpoint of preparing a uniform varnish that gives thin films having a high flatness, the molecular weight is preferably not more than 6,000, more preferably not more than 5,000, even more preferably not more than 4,000, and still more preferably not more than 3,000.

Of the above charge-transporting oligomers, taking into account the balance between the solubility in organic solvents and the charge transportability of the resulting thin film, aniline derivatives are preferred. Exemplary aniline derivatives include the oligoaniline derivatives mentioned in JP-A 2002-151272, the oligoaniline compounds mentioned in WO 2004/105446, the oligoaniline compounds mentioned in WO 2008/032617, the oligoaniline compounds mentioned in WO 2008/032616, and the aryldiamine compounds mentioned in WO 2013/042623.

Preferred use can be made of the aniline derivatives of formula (3) below.

tynyl, 1-methyl-2-propynyl, n-1-pentynyl, n-2-pentynyl, n-3-pentynyl, n-4-pentynyl, 1-methyl-n-butynyl, 2-methyl-n-butynyl, 3-methyl-n-butynyl, 1,1-dimethyl-n-propynyl, n-1-hexynyl, n-1-decynyl, n-1-pentadecynyl and n-1-eicosynyl groups.

Specific examples of the aryl group of 6 to 20 carbon atoms include phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl groups.

Specific examples of the heteroaryl group of 2 to 20 carbon atoms include 2-thienyl, 3-thienyl, 2-furanyl, 3-furanyl, 2-oxazolyl, 4-oxazolyl, 5-oxazolyl, 3-isooxazolyl, 4-isooxazolyl, 5-isooxazolyl, 2-thiazolyl, 4-thiazolyl, 5-thiazolyl, 3-isothiazolyl, 4-isothiazolyl, 5-isothiazolyl, 2-imidazolyl, 4-imidazolyl, 2-pyridyl, 3-pyridyl and 4-pyridyl groups.

$R^{107}$ and $R^{108}$ are each independently a hydrogen atom, a chlorine atom, a bromine atom, an iodine atom, a nitro group, a cyano group, an amino group, an aldehyde group, a hydroxyl group, a thiol group, a sulfonic acid group, a carboxyl group, an alkyl group of 1 to 20 carbon atoms, alkenyl group of 2 to 20 carbon atoms or alkynyl group of 2 to 20 carbon atoms which may be substituted with $Z^1$, an aryl group of 6 to 20 carbon atoms or heteroaryl group of 2

[Chem. 4]

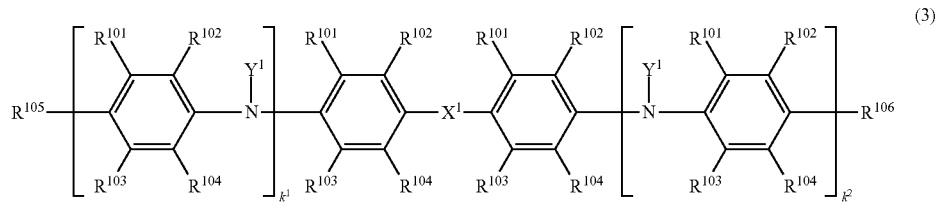

(3)

In formula (3), $X^1$ represents —$NY^1$—, —O—, —S—, —$(CR^{107}R^{108})_L$— or a single bond. When $k^1$ or $k^2$ is 0, $X^1$ represents —$NY^1$—.

Each $Y^1$ is independently a hydrogen atom, an alkyl group of 1 to 20 carbon atoms, alkenyl group of 2 to 20 carbon atoms or alkynyl group of 2 to 20 carbon atoms which may be substituted with $Z^1$, or an aryl group of 6 to 20 carbon atoms or heteroaryl group of 2 to 20 carbon atoms which may be substituted with $Z^2$.

The alkyl group of 1 to 20 carbon atoms may be linear, branched or cyclic. Specific examples include linear or branched alkyl groups of 1 to 20 carbon atoms such as methyl, ethyl, n-propyl, isopropyl, n-butyl, isobutyl, s-butyl, tert-butyl, n-pentyl, n-hexyl, n-heptyl, n-octyl, n-nonyl and n-decyl groups; and cyclic alkyl groups of 3 to 20 carbon atoms such as cyclopropyl, cyclobutyl, cyclopentyl, cyclohexyl, cycloheptyl, cyclooctyl, cyclononyl, cyclodecyl, bicyclobutyl, bicyclopentyl, bicyclohexyl, bicycloheptyl, bicyclooctyl, bicyclononyl and bicyclodecyl groups.

The alkenyl group of 2 to 20 carbon atoms may be linear, branched or cyclic. Specific examples include ethenyl, n-1-propenyl, n-2-propenyl, 1-methylethenyl, n-1-butenyl, n-2-butenyl, n-3-butenyl, 2-methyl-1-propenyl, 2-methyl-2-propenyl, 1-ethylethenyl, 1-methyl-1-propenyl, 1-methyl-2-propenyl, n-1-pentenyl, n-1-decenyl and n-1-eicosenyl groups.

The alkynyl group of 2 to 20 carbon atoms may be linear, branched or cyclic. Specific examples include ethynyl, n-1-propynyl, n-2-propynyl, n-1-butynyl, n-2-butynyl, n-3-buto 20 carbon atoms which may be substituted with $Z^2$, or —$NHY^2$, —$NY^3Y^4$, —$C(O)Y^5$, —$OY^6$, —$SY^7$, —$SO_3Y^8$, —$C(O)OY^9$, —$OC(O)Y^{10}$, —$C(O)NHY^{11}$ or —$C(O)NY^{12}Y^{13}$.

$Y^2$ to $Y^{13}$ are each independently an alkyl group of 1 to 20 carbon atoms, alkenyl group of 2 to 20 carbon atoms or alkynyl group of 2 to 20 carbon atoms which may be substituted with $Z^1$, or an aryl group of 6 to 20 carbon atoms or heteroaryl group of 2 to 20 carbon atoms which may be substituted with $Z^2$.

$Z^1$ is a chlorine atom, a bromine atom, an iodine atom, a nitro group, a cyano group, an amino group, an aldehyde group, a hydroxyl group, a thiol group, a sulfonic acid group, a carboxyl group, or an aryl group of 6 to 20 carbon atoms or heteroaryl group of 2 to 20 carbon atoms which may be substituted with $Z^3$.

$Z^2$ is a chlorine atom, a bromine atom, an iodine atom, a nitro group, a cyano group, an amino group, an aldehyde group, a hydroxyl group, a thiol group, a sulfonic acid group, a carboxyl group, or an alkyl group of 1 to 20 carbon atoms, alkenyl group of 2 to 20 carbon atoms or alkynyl group of 2 to 20 carbon atoms which may be substituted with $Z^3$.

$Z^3$ is a chlorine atom, a bromine atom, an iodine atom, a nitro group, a cyano group, an amino group, an aldehyde group, a hydroxyl group, a thiol group, a sulfonic acid group or a carboxyl group.

The alkyl, alkenyl, alkynyl, aryl and heteroaryl groups on $R^{107}$, $R^{108}$ and $Y^2$ to $Y^{13}$ are exemplified in the same way as described above.

Of these, $R^{107}$ and $R^{108}$ are preferably hydrogen atoms or alkyl groups of 1 to 20 carbon atoms which may be substituted with $Z^1$, more preferably hydrogen atoms or methyl groups which may be substituted with $Z^1$, and most preferably both hydrogen atoms.

L, which represents the number of divalent groups of the formula —$(CR^{107}R^{108})$—, is an integer from 1 to 20, preferably from 1 to 10, more preferably from 1 to 5, even more preferably 1 or 2, and most preferably 1. When L is 2 or more, the plurality of $R^{107}$ groups may be mutually the same or different, and the plurality of $R^{108}$ may be mutually the same or different.

In particular, $X^1$ is preferably —$NY^1$— or a single bond. $Y^1$ is preferably a hydrogen atom or an alkyl group of 1 to 20 carbon atoms which may be substituted with $Z'$, more preferably a hydrogen atom or a methyl group which may be substituted with $Z'$, and most preferably a hydrogen atom.

In formula (3), $R^{101}$ to $R^{106}$ are each independently a hydrogen atom, a chlorine atom, a bromine atom, an iodine atom, a nitro group, a cyano group, an amino group, an aldehyde group, a hydroxyl group, a thiol group, a sulfonic acid group, a carboxyl group, an alkyl group of 1 to 20 carbon atoms, alkenyl group of 2 to 20 carbon atoms or alkynyl group of 2 to 20 carbon atoms which may be substituted with $Z'$, an aryl group of 6 to 20 carbon atoms or heteroaryl group of 2 to 20 carbon atoms which may be substituted with $Z^2$, or —$NHY^2$, —$NY^3Y^4$, —$C(O)Y^5$, —$OY^6$, —$SY^7$, —$SO_3Y^8$, —$C(O)OY^9$, —$OC(O)Y^{10}$, —$C(O)NHY^{11}$ or —$C(O)NY^{12}Y^{13}$ (wherein $Y^2$ to $Y^{13}$ are as defined above). These alkyl, alkenyl, alkynyl, aryl and heteroaryl groups are exemplified in the same way as above.

In particular, in formula (3), $R^{101}$ to $R^{104}$ are each preferably a hydrogen atom, a halogen atom, an alkyl group of 1 to 10 carbon atoms which may be substituted with $Z^1$, or an aryl group of 6 to 14 carbon atoms which may be substituted with $Z^2$; more preferably a hydrogen atom or an alkyl group of 1 to 10 carbon atoms; and most preferably are all hydrogen atoms.

$R^{105}$ and $R^{106}$ are each preferably a hydrogen atom, a chlorine atom, a bromine atom, an iodine atom, an alkyl group of 1 to 10 carbon atoms which may be substituted with $Z^1$, an aryl group of 6 to 14 carbon atoms which may be substituted with $Z^2$, or a diphenylamino group which may be substituted with $Z^2$ (the phenyl group —$NY^3Y^4$ wherein $Y^3$ and $Y^4$ may be substituted with $Z^2$); are more preferably a hydrogen atom or a diphenylamino group; and are even more preferably both hydrogen atoms or both diphenylamino groups.

Of these, a combination in which $R^{101}$ to $R^{104}$ are each preferably a hydrogen atom or an alkyl group of 1 to 10 carbon atoms, $R^{105}$ and $R^{106}$ are each a hydrogen atom or a diphenylamino group, $X^1$ is —$NY^1$— or a single bond and $Y^1$ is a hydrogen atom or a methyl group is preferred; and a combination in which $R^{101}$ to $R^{104}$ are each a hydrogen atom, $R^{105}$ and $R^{106}$ are both hydrogen atoms or diphenylamino groups, and $X^1$ is —NH— or a single bond is more preferred.

In formula (3), $k^1$ and $k^2$ are each independently an integer of 0 or more and together satisfy the condition $1 \leq k^1+k^2$ 20. Taking into account the balance between the charge transportability of the resulting thin film and the solubility of the aniline derivative, they preferably satisfy the condition $2 \leq k^1+k^2 \leq 8$, more preferably satisfy the condition $2 \leq k^1+k^2 \leq 6$, and even more preferably satisfy the condition $2 \leq k^1+k^2 \leq 4$.

In $Y^1$ to $Y^{13}$ and $R^{101}$ to $R^{108}$, $Z^1$ is preferably a chlorine atom, a bromine atom, an iodine atom or an aryl group of 6 to 20 carbon atoms which may be substituted with $Z^3$; more preferably a chlorine atom, a bromine atom, an iodine atom or a phenyl group which may be substituted with $Z^3$; and most preferably does not exist (i.e., is non-substituting).

$Z^2$ is preferably a chlorine atom, a bromine atom, an iodine atom or an alkyl group of 1 to 20 carbon atoms which may be substituted with $Z^3$, more preferably a chlorine atom, a bromine atom, an iodine atom or an alkyl group of 1 to 4 carbon atoms which may be substituted with $Z^3$; and most preferably does not exist (i.e., is non-substituting).

$Z^3$ is preferably a chlorine atom, a bromine atom or an iodine atom; and most preferably does not exist (i.e., is non-substituting).

In $Y^1$ to $Y^{13}$ and $R^{101}$ to $R^{108}$, the number of carbon atoms on the alkyl, alkenyl and alkynyl groups is preferably 10 or less, more preferably 6 or less, and even more preferably 4 or less. The number of carbon atoms on the aryl and heteroaryl groups is preferably 14 or less, more preferably 10 or less, and even more preferably 6 or less.

The method of synthesizing the aniline derivative is exemplified by, without particular limitation, the methods described in *Bulletin of Chemical Society of Japan*, 67, pp. 1749-1752 (1994); *Synthetic Metals*, 84, pp. 119-120 (1997); *Thin Solid Films*, 520(24), pp. 7157-7163 (2012); and WO 2008/032617, WO 2008/032616, WO 2008/129947 and WO 2013/084664.

Specific examples of the aniline derivative of formula (3) include, but are not limited to, those of the following formulas. In the formulas below, "DPA" stands for a diphenylamino group, "Ph" stands for a phenyl group, and "TPA" stands for a p-(diphenylamino)phenyl group.

[Chem. 5]

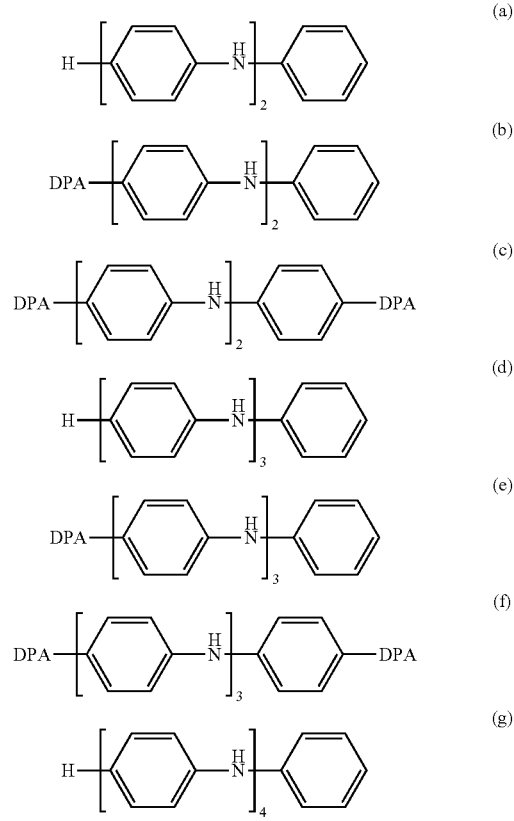

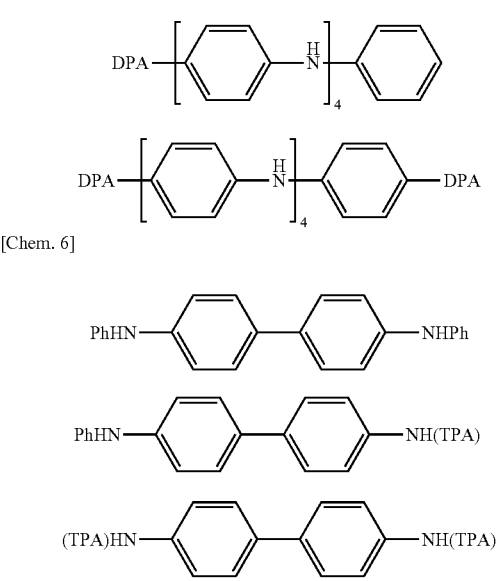

[Organic Solvent]

A high-solvency solvent capable of dissolving well the above aniline derivative and the sulfonic acid ester compound of the invention may be used as the organic solvent employed when preparing the charge-transporting varnish of the invention. In particular, because the sulfonic acid ester compound of the invention has a high solubility in low-polarity solvents, it is possible to use a low-polarity solvent as the high-solvency solvent.

Among high-solvency solvents, specific examples of low-polarity solvents include chlorinated solvents such as chloroform and chlorobenzene; and aromatic hydrocarbon solvents such as toluene, xylene, tetralin, cyclohexylbenzene and 3-phenoxytoluene. Specific examples of polar solvents include amide solvents such as N,N-dimethylformamide, N,N-dimethylacetamide, N,N-dimethylisobutyramide, N-methylpyrrolidone and 1,3-dimethyl-2-imidazolidinone; ketone solvents such as isophorone and cyclohexanone; ester solvents such as ethyl acetate and methyl benzoate; polyhydric alcohol solvents such as ethylene glycol and diethylene glycol; ether solvents such as tetrahydrofuran, dioxane and anisole; and sulfoxide solvents such as dimethylsulfoxide. These solvents may be used singly or two or more may be used in admixture. The amount of such solvents used may be set to from 5 to 100 wt % of the overall solvent used in the varnish.

It is preferable for all the charge-transporting substances to be in a completely dissolved or uniformly dispersed state in the above solvent, and more preferable for them to be completely dissolved.

The organic solvent may include at least one high-viscosity organic solvent having a viscosity at 25° C. of from 10 to 200 mPa·s, especially from 35 to 150 mPa·s, and a boiling point at standard pressure (atmospheric pressure) of from 50 to 300° C., especially from 150 to 250° C. Adding such a solvent makes the viscosity of the varnish easy to adjust, as a result of which it is possible to prepare a varnish which reproducibly gives thin films of high flatness and is suitable for the method of application used.

Examples of high-viscosity organic solvents include, but are not limited to, cyclohexanol, ethylene glycol, ethylene glycol diglycidyl ether, 1,3-octylene glycol, diethylene glycol, dipropylene glycol, triethylene glycol, tripropylene glycol, 1,3-butanediol, 2,3-butanediol, 1,4-butanediol, propylene glycol and hexylene glycol. The high-viscosity organic solvent may also serve as a high-solvency solvent. These are determined by the type of host.

The high-viscosity organic solvent is added in a proportion that is preferably in a range within which the deposition of solids does not occur. An addition ratio of from 5 to 90 wt % based on the overall solvent used in the varnish is preferred, so long as solids do not deposit out.

In addition, other solvents may also be admixed in a ratio with respect to the overall solvent used in the varnish of from 1 to 90 wt %, and preferably from 1 to 50 wt %, for such purposes as to increase the wettability on a substrate and to adjust the surface tension, polarity and boiling point of the solvent.

Examples of such solvents include, but are not limited to, propylene glycol monomethyl ether, ethylene glycol monobutyl ether, diethylene glycol diethyl ether, diethylene glycol monomethyl ether, diethylene glycol dimethyl ether, diethylene glycol monoethyl ether acetate, diethylene glycol monobutyl ether acetate, dipropylene glycol monomethyl ether, propylene glycol monomethyl ether acetate, diethylene glycol monoethyl ether, diacetone alcohol, γ-butyrolactone, ethyl lactate and n-hexyl acetate. These solvents may be used singly or two or more may be used in admixture. These solvents, which may also serve as high-solvency solvents, are determined by the type of host.

In this invention, from the standpoint of reproducibly obtaining thin films having a higher flatness, it is desirable for the charge-transporting varnish to be obtained by dissolving the charge-transporting substance in the organic solvent and subsequently filtering the solution using a sub-micron-order filter or the like.

The solids concentration in the varnish of the invention, from the standpoint of ensuring a sufficient film thickness while minimizing deposition of the charge-transporting substance, is generally from about 0.1 wt % to about 20 wt %, and preferably from 0.5 to 10 wt %. As used herein, "solids" refers to the constituents that remain when the solvent is removed from the ingredients included in the varnish. The viscosity of the inventive varnish is generally from 1 to 50 mPa·s at 25° C.

The content of the electron-accepting substance precursor within these solids, expressed as a molar ratio with respect to unity (1) for the charge-transporting substance, is preferably from about 0.01 to about 20, and more preferably from about 0.05 to about 10.

[Charge-Transporting Thin Film]

A charge-transporting thin film can be formed on a substrate by applying the charge-transporting varnish of the invention onto the substrate and drying the applied varnish.

Examples of the varnish coating method include, but are not limited to, dipping, spin coating, transfer printing, roll coating, brush coating, inkjet coating, spraying and slit coating. It is preferable for the viscosity and surface tension of the varnish to be adjusted according to the coating method.

When using the varnish of the invention, the liquid film drying conditions are not particularly limited; one example is heating and baking on a hot plate. A dry film can be obtained by heating and baking in a temperature range of generally from about 100° C. to about 260° C. for a period of from about 1 minute to about 1 hour. The baking atmosphere also is not particularly limited.

The thickness of the charge-transporting thin film is not particularly limited. However, when the thin film is to be used as a functional layer in an organic EL device, a film thickness of from 5 to 200 nm is preferred. Methods for changing the film thickness include, for example, changing the solids concentration in the varnish and changing the amount of solution on the substrate at the time of application.

[Organic EL Device]

The organic EL device of the invention has a pair of electrodes and additionally has, between these electrodes, the above-described charge-transporting thin film of the invention.

Typical organic EL device configurations include, but are not limited to, configurations (a) to (f) below. In these configurations, where necessary, an electron-blocking layer or the like may be provided between the light-emitting layer and the anode, and a hole-blocking layer or the like may be provided between the light-emitting layer and the cathode. Alternatively, the hole-injecting layer, hole-transporting layer or hole-injecting-and-transporting layer may also have the function of, for example, an electron-blocking layer; and the electron-injecting layer, electron-transporting layer or electron-injecting-and-transporting layer may also have the function of, for example, a hole-blocking layer.

(a) anode/hole-injecting layer/hole-transporting layer/light-emitting layer/electron-transporting layer/electron-injecting layer/cathode
(b) anode/hole-injecting layer/hole-transporting layer/light-emitting layer/electron-injecting-and-transporting layer/cathode
(c) anode/hole-injecting-and-transporting layer/light-emitting layer/electron-transporting layer/electron-injecting layer/cathode
(d) anode/hole-injecting-and-transporting layer/light-emitting layer/electron-injecting-and-transporting layer/cathode
(e) anode/hole-injecting layer/hole-transporting layer/light-emitting layer/cathode
(f) anode/hole-injecting-and-transporting layer/light-emitting layer/cathode As used herein, "hole-injecting layer," "hole-transporting layer" and "hole-injecting-and-transporting layer" refer to layers which are formed between the light-emitting layer and the anode and which have the function of transporting holes from the anode to the light-emitting layer. When only one layer of hole-transporting material is provided between the light-emitting layer and the anode, this is a "hole-injecting-and-transporting layer"; when two or more layers of hole-transporting material are provided between the light-emitting layer and the anode, the layer that is closer to the anode is a "hole-injecting layer" and the other layer is a "hole-transporting layer." In particular, thin films having not only an excellent ability to accept holes from the anode but also an excellent ability to inject holes into, respectively, the hole-transporting layer and the light-emitting layer may be used as the hole-injecting layer and the hole-injecting-and-transporting layer.

In addition, "electron-injecting layer," "electron-transporting layer" and "electron-injecting-and-transporting layer" refer to layers which are formed between the light-emitting layer and the cathode and which have the function of transporting electrons from the cathode to the light-emitting layer. When only one layer of electron-transporting material is provided between the light-emitting layer and the cathode, this is an "electron-injecting-and-transporting layer"; when two or more layers of electron-transporting material are provided between the light-emitting layer and the cathode, the layer that is closer to the cathode is an "electron-injecting layer" and the other layer is an "electron-transporting layer."

The "light-emitting layer" is an organic layer having a light-emitting function. When a doping system is used, this layer includes a host material and a dopant material. The function of the host material is primarily to promote the recombination of electrons and holes and to confine the resulting excitons within the light-emitting layer. The function of the dopant material is to cause the excitons obtained by recombination to efficiently luminesce. In the case of phosphorescent devices, the host material functions primarily to confine within the light-emitting layer the excitons generated by the dopant.

The materials and method employed to produce an organic EL device using the charge-transporting varnish of the invention are exemplified by, but not limited to, those described below.

The electrode substrate to be used is preferably cleaned beforehand by liquid washing with, for example, a cleaning agent, alcohol or pure water. For example, when the electrode substrate is an anode substrate, it is preferably subjected to surface treatment such as UV/ozone treatment or oxygen-plasma treatment just prior to use. However, surface treatment need not be carried out in cases where the anode material is composed primarily of organic substances.

An example is described below of a method for producing the organic EL device of the invention in which a thin-film obtained from the charge-transporting varnish of the invention serves as the hole-injecting layer.

Using the above-described method, a hole-injecting layer is formed on an electrode by applying the charge-transporting varnish of the invention onto an anode substrate and then baking the applied varnish. A hole-transporting layer, a light-emitting layer, an electron-transporting layer, an electron-injecting layer and a cathode are provided in this order on the hole-injecting layer. The hole-transporting layer, light-emitting layer, electron-transporting layer and electron-injecting layer may be formed by either a vapor deposition process or a coating process (wet process), depending on the properties of the material used.

Illustrative examples of anode materials include transparent electrodes such as indium-tin oxide (ITO) and indium-zinc oxide (IZO), and metal anodes made of a metal such as aluminum or an alloy of such a metal. An anode material on which planarizing treatment has been carried out is preferred. Use can also be made of polythiophene derivatives and polyaniline derivatives having a high charge transportability.

Examples of other metals that may make up the metal anode include, but are not limited to, scandium, titanium, vanadium, chromium, manganese, iron, cobalt, nickel, copper, zinc, gallium, yttrium, zirconium, niobium, molybdenum, ruthenium, rhodium, palladium, cadmium, indium, lanthanum, cerium, praseodymium, neodymium, promethium, samarium, europium, gadolinium, terbium, dysprosium, holmium, erbium, thulium, ytterbium, hafnium, thallium, tungsten, rhenium, osmium, iridium, platinum, gold, titanium, lead, bismuth, and alloys thereof.

Specific examples of hole-transporting layer-forming materials include the following hole-transporting low-molecular-weight materials: triarylamines such as (triphenylamine) dimer derivatives, [(triphenylamine) dimer] spirodimer,
N,N'-bis(naphthalen-1-yl)-N,N'-bis(phenyl)benzidine (α-NPD),
N,N'-bis(naphthalen-2-yl)-N,N'-bis(phenyl)benzidine,
N,N'-bis(3-methylphenyl)-N,N'-bis(phenyl)benzidine,
N,N'-bis(3-methylphenyl)-N,N'-bis(phenyl)-9,9-spirobifluorene, N,N'-bis(naphthalen-1-yl)-N,N'-bis(phenyl)-9,9-spirobifluorene,
N,N'-bis(3-methylphenyl)-N,N'-bis(phenyl)-9,9-dimethylfluorene,
N,N'-bis(naphthalen-1-yl)-N,N'-bis(phenyl)-9,9-dimethylfluorene,
N,N'-bis(3-methylphenyl)-N,N'-bis(phenyl)-9,9-diphenylfluorene,
N,N'-bis(naphthalen-1-yl)-N,N'-bis(phenyl)-9,9-diphenylfluorene,
N,N'-bis(naphthalen-1-yl)-N,N'-bis(phenyl)-2,2'-dimethylbenzidine,
2,2',7,7'-tetrakis(N,N-diphenylamino)-9,9-spirobifluorene,
9,9-bis[4-(N,N-bis-biphenyl-4-ylamino)phenyl]-9H-fluorene,
9,9-bis[4-(N,N-bisnaphthalen-2-ylamino)phenyl]-9H-fluorene,
9,9-bis[4-(N-naphthalen-1-yl-N-phenylamino)phenyl]-9H-fluorene,
2,2',7,7'-tetrakis[N-naphthalenyl(phenyl)amino]-9,9-spirobifluorene,
N,N'-bis(phenanthren-9-yl)-N,N'-bis(phenyl)benzidine,
2,2'-bis[N,N-bis(biphenyl-4-yl)amino]-9,9-spirobifluorene,
2,2'-bis(N,N-diphenylamino)-9,9-spirobifluorene,
di[4-(N,N-di(p-tolyl)amino)phenyl]cyclohexane,
2,2',7,7'-tetra(N,N-di(p-tolyl))amino-9,9-spirobifluorene,
N,N,N',N'-tetra-naphthalen-2-yl-benzidine,
N,N,N',N'-tetra(3-methylphenyl)-3,3'-dimethylbenzidine,
N,N'-di(naphthalenyl)-N,N'-di(naphthalen-2-yl)benzidine,
N,N,N',N'-tetra(naphthalenyl)benzidine,
N,N'-di(naphthalen-2-yl)-N,N'-diphenylbenzidine-1-4-diamine,
$N^1,N^4$-diphenyl-$N^1,N^4$-di(m-tolyl)benzene-1,4-diamine,
$N^2,N^2,N^6,N^6$-tetraphenylnaphthalene-2,6-diamine, tris(4-(quinolin-8-yl)phenyl)amine,
2,2'-bis(3-(N,N-di(p-tolyl)amino)phenyl)biphenyl,
4,4',4"-tris[3-methylphenyl(phenyl)amino]triphenylamine (m-MTDATA) and
4,4',4"-tris[1-naphthyl(phenyl)amino]triphenylamine (1-TNATA); and oligothiophenes such as
5,5"-bis-{4-[bis(4-methylphenyl)amino]phenyl}-2,2':5',2"-terthiophene (BMA-3T).

Specific examples of light-emitting layer-forming materials include
tris(8-quinolinolate) aluminum(III) (Alq$_3$), bis(8-quinolinolate) zinc(II) (Znq$_2$),
bis(2-methyl-8-quinolinolate)-4-(p-phenylphenolate) aluminum(III) (BAlq),
4,4'-bis(2,2-diphenylvinyl)biphenyl, 9,10-di(naphthalen-2-yl)anthracene,
2-tert-butyl-9,10-di(naphthalen-2-yl)anthracene,
2,7-bis[9,9-di(4-methylphenyl)-fluoren-2-yl]-9,9-di(4-methylphenyl)fluorene,
2-methyl-9,10-bis(naphthalen-2-yl)anthracene,
2-(9,9-spirobifluoren-2-yl)-9,9-spirobifluorene,
2,7-bis(9,9-spirobifluoren-2-yl)-9,9-spirobifluorene,
2-[9,9-di(4-methylphenyl)-fluoren-2-yl]-9,9-di(4-methylphenyl)fluorene,
2,2'-dipyrenyl-9,9-spirobifluorene, 1,3,5-tris(pyren-1-yl)benzene,
9,9-bis[4-(pyrenyl)phenyl]-9H-fluorene, 2,2'-bi(9,10-diphenylanthracene),
2,7-dipyrenyl-9,9-spirobifluorene, 1,4-di(pyren-1-yl)benzene,
1,3-di(pyren-1-yl)benzene, 6,13-di(biphenyl-4-yl)pentacene,
3,9-di(naphthalen-2-yl)perylene, 3,10-di(naphthalen-2-yl)perylene,
tris[4-(pyrenyl)-phenyl]amine, 10,10'-di(biphenyl-4-yl)-9,9'-bianthracene,
N,N'-di(naphthalen-1-yl)-N,N'-diphenyl-[1,1':4',1":4",1"'-quaterphenyl]-4,4"'-diamine,
4,4'-di[10-(naphthalen-1-yl)anthracen-9-yl]biphenyl,
dibenzo{[f,f']-4,4',7,7'-tetraphenyl}diindeno[1,2,3-cd:1',2',3'-lm]perylene,
1-(7-(9,9'-bianthracen-10-yl)-9,9-dimethyl-9H-fluoren-2-yl)pyrene,
1-(7-(9,9'-bianthracen-10-yl)-9,9-dihexyl-9H-fluoren-2-yl)pyrene,
1,3-bis(carbazol-9-yl)benzene, 1,3,5-tris(carbazol-9-yl)benzene,
4,4',4"-tris(carbazol-9-yl)triphenylamine, 4,4'-bis(carbazol-9-yl)biphenyl (CBP),
4,4'-bis(carbazol-9-yl)-2,2'-dimethylbiphenyl,
2,7-bis(carbazol-9-yl)-9,9-dimethylfluorene,
2,2',7,7'-tetrakis(carbazol-9-yl)-9,9-spirobifluorene,
2,7-bis(carbazol-9-yl)-9,9-di(p-tolyl)fluorene, 9,9-bis[4-(carbazol-9-yl)-phenyl]fluorene,
2,7-bis(carbazol-9-yl)-9,9-spirobifluorene, 1,4-bis(triphenylsilyl)benzene,
1,3-bis(triphenylsilyl)benzene,
bis(4-N,N-diethylamino-2-methylphenyl)-4-methylphenylmethane,
2,7-bis(carbazol-9-yl)-9,9-dioctylfluorene, 4,4"-di(triphenylsilyl)-p-terphenyl,
4,4'-di(triphenylsilyl)biphenyl, 9-(4-tert-butylphenyl)-3,6-bis(triphenylsilyl)-9H-carbazole,
9-(4-tert-butylphenyl)-3,6-ditrityl-9H-carbazole,
9-(4-tert-butylphenyl)-3,6-bis(9-(4-methoxyphenyl)-9H-fluoren-9-yl)-9H-carbazole,
2,6-bis(3-(9H-carbazol-9-yl)phenyl)pyridine,
triphenyl(4-(9-phenyl-9H-fluoren-9-yl)phenyl)silane,
9,9-dimethyl-N,N-diphenyl-7-(4-(1-phenyl-1H-benzo[d]imidazol-2-yl)phenyl-9H-fluoren-2-amine,
3,5-bis(3-(9H-carbazol-9-yl)phenyl)pyridine,
9,9-spirobifluoren-2-yl-diphenyl-phosphine oxide,
9,9'-(5-triphenylsilyl)-1,3-phenylene)bis(9H-carbazole),
3-(2,7-bis(diphenylphosphoryl)-9-phenyl-9H-fluoren-9-yl)-9-phenyl-9H-carbazole,
4,4,8,8,12,12-hexa(p-tolyl)-4H-8H-12H-12C-azadibenzo[cd,mn]pyrene,
4,7-di(9H-carbazol-9-yl)-1,10-phenanthroline, 2,2'-bis(4-(carbazol-9-yl)phenyl)biphenyl,
2,8-bis(diphenylphosphoryl)dibenzo[b,d]thiophene, bis(2-methylphenyl)diphenylsilane,
bis[3,5-di(9H-carbazol-9-yl)phenyl]diphenylsilane,
3,6-bis(carbazol-9-yl)-9-(2-ethylhexyl)-9H-carbazole,
3-(diphenylphosphoryl)-9-(4-(diphenylphosphoryl)phenyl)-9H-carbazole and
3,6-bis[(3,5-diphenyl)phenyl]-9-phenylcarbazole.

The light-emitting layer may be formed by the co-vapor deposition of these materials with a light-emitting dopant.

Specific examples of light-emitting dopants include
3-(2-benzothiazolyl)-7-(diethylamino)coumarin,
2,3,6,7-tetrahydro-1,1,7,7-tetramethyl-1H,5H,11H-10-(2-benzothiazolyl)quinolidino-[9,9a,1gh]coumarin,
quinacridone, N,N'-dimethylquinacridone, tris(2-phenylpyridine) iridium(III) (Ir(ppy)$_3$),
bis(2-phenylpyridine)(acetylacetonate) iridium(III) (Ir(ppy)$_2$(acac)),
tris[2-(p-tolyl)pyridine] iridium(III) (Ir(mppy)$_3$), 9,10-bis[N,N-di(p-tolyl)amino]anthracene,
9,10-bis[phenyl(m-tolyl)amino]anthracene, bis[2-(2-hydroxyphenyl)benzothiazolate] zinc(II),
$N^{10},N^{10},N^{10},N^{10}$-tetra(p-tolyl)-9,9'-bianthracene-10,10'-diamine,
$N^{10},N^{10},N^{10},N^{10}$-tetraphenyl-9,9'-bianthracene-10,10'-diamine,
$N^{10},N^{10}$-diphenyl-$N^{10},N^{10}$-dinaphthalenyl-9,9'-bianthracene-10,10'-diamine,
4,4'-bis(9-ethyl-3-carbazovinylene)-1,1'-biphenyl, perylene,
2,5,8,11-tetra-tert-butylperylene, 1,4-bis[2-(3-N-ethylcarbazolyl)vinyl]benzene,
4,4'-bis[4-(di-p-tolylamino)styryl]biphenyl,
4-(di-p-tolylamino)-4'-[(di-p-tolylamino)styryl]stilbene,
bis[3,5-difluoro-2-(2-pyridyl)phenyl-(2-carboxypyridyl)] iridium(III),
4,4'-bis[4-(diphenylamino)styryl]biphenyl,
bis(2,4-difluorophenylpyridinato)tetrakis(1-pyrazolyl)borate iridium(III),
N,N'-bis(naphthalen-2-yl)-N,N'-bis(phenyl)-tris(9,9-dimethylfluorenylene),
2,7-bis {2-[phenyl(m-tolyl)amino]-9,9-dimethylfluoren-7-yl}-9,9-dimethylfluorene,
N-(4-((E)-2-(6((E)-4-(diphenylamino)styryl)naphthalen-2-yl)vinyl)phenyl)-N-phenylbenzenamine,
fac-iridium(III) tris(1-phenyl-3-methylbenzimidazolin-2-ylidene-C,$C^2$),
mer-iridium(III) tris(1-phenyl-3-methylbenzimidazolin-2-ylidene-C,$C^2$),
2,7-bis[4-(diphenylamino)styryl]-9,9-spirobifluorene,
6-methyl-2-(4-(9-(4-(6-methylbenzo[d]thiazol-2-yl)phenyl)anthracen-10-yl)phenyl)benzo-[d]thiazole,
1,4-di[4-(N,N-diphenyeamino]styrylbenzene, 1,4-bis(4-(9H-carbazol-9-yl)styryl)benzene,
(E)-6-(4-(diphenylamino)styryl)-N,N-diphenylnaphthalen-2-amine,
bis(2,4-difluorophenylpyridinato)(5-(pyridin-2-yl)-1H-tetrazolate) iridium(III),
bis(3-trifluoromethyl-5-(2-pyridyl)pyrazole)((2,4-difluorobenzyl)diphenylphosphinate) iridium(III),
bis(3-trifluoromethyl-5-(2-pyridyl)pyrazolate)(benzyldiphenylphosphinate) iridium(III),
bis(1-(2,4-difluorobenzyl)-3-methythenzimidazolium)(3-(trifluoromethyl)-5-(2-pyridyl)-1,2,4-triazolate) iridium (III),
bis(3-trifluoromethyl-5-(2-pyridyl)pyrazolate)(4',6'-difluorophenylpyridinate) iridium(III),
bis(4',6'-difluorophenylpyridinato)(3,5-bis(trifluoromethyl)-2-(2'-pyridyl)pyrrolate) iridium(III),
bis(4',6'-difluorophenylpyridinato)(3-(trifluoromethyl)-5-(2-pyridyl)-1,2,4-triazolate) iridium (III),
(Z)-6-mesityl-N-(6-mesitylquinolin-2(1H)-ylidene)quinoline-2-amine-BF2,
(E)-2-(2-(4-(dimethylamino)styryl)-6-methyl-4H-pyran-4-ylidene)malononitrile,
4-(dicyanomethylene)-2-methyl-6-julolidyl-9-enyl-4H-pyran,
4-(dicyanomethylene)-2-methyl-6-(1,1,7,7-tetramethyljulolidyl-9-enyl)-4H-pyran,
4-(dicyanomethylene)-2-tert-butyl-6-(1,1,7,7-tetramethyljulolidin-4-ylvinyl)-4H-pyran,
tris(dibenzoylmethane)phenanthroline europium(III), 5,6,11,12-tetraphenylnaphthacene,
bis(2-benzo[b]thiophen-2-yl-pyridine)(acetylacetonate) iridium(III),
tris(1-phenylisoquinoline) iridium(III),
bis(1-phenylisoquinoline)(acetylacetonate) iridium(III),
bis[1-(9,9-dimethyl-9H-fluoren-2-yl)isoquinoline](acetylacetonate) iridium(III),
bis[2-(9,9-dimethyl-9H-fluoren-2-yl)quinoline](acetylacetonate) iridium(III),
tris[4,4'-di-tert-butyl-(2,2')-bipyridine] ruthenium(III)•bis(hexafluorophosphate),
tris(2-phenylquinoline) iridium(III), bis(2-phenylquinoline)(acetylacetonate) iridium(III),
2,8-di-tert-butyl-5,11-bis(4-tert-butylphenyl)-6,12-diphenyltetracene,
bis(2-phenylbenzothiazolate)(acetylacetonate) iridium(III),
platinum 5,10,15,20-tetraphenyltetrabenzoporphyrin,
osmium(II) bis(3-trifluoromethyl-5-(2-pyridine)pyrazolate) dimethylphenylphosphine,
osmium(II) bis(3-trifluoromethyl)-5-(4-tert-butylpyridyl)-1,2,4-triazolate)-diphenylmethylphosphine,
osmium(II) bis(3-(trifluoromethyl)-5-(2-pyridyl)-1,2,4-triazole)dimethylphenylphosphine,
osmium(II) bis(3-(trifluoromethyl)-5-(4-tert-butylpyridyl)-1,2,4-triazolate)-dimethylphenylphosphine,
bis[2-(4-n-hexylphenyl)quinoline](acetylacetonate) iridium (III),
tris[2-(4-n-hexylphenyl)quinoline] iridium(III),
tris[2-phenyl-4-methylquinoline] iridium(III),
bis(2-phenylquinoline)(2-(3-methylphenyl)pyridinate) iridium(III),
bis(2-(9,9-diethylfluoren-2-yl)-1-phenyl-1H-benzo[d]imidazolato)(acetylacetonate) iridium(III),
bis(2-phenylpyridine)(3-(pyridin-2-yl)-2H-chromen-9-onate) iridium(III),
bis(2-phenylquinoline)(2,2,6,6-tetramethylheptane-3,5-dionate) iridium(III),
bis(phenylisoquinoline)(2,2,6,6-tetramethylheptane-3,5-dionate) iridium(III),
iridium(III) bis(4-phenylthieno[3,2-c]pyridinato-N,$C^2$) acetylacetonate,
(E)-2-(2-tert-butyl-6-(2-(2,6,6-trimethyl-2,4,5,6-tetrahydro-1H-pyrrolo[3,2,1-ij]quinolin-8-yl)vinyl)-4H-pyran-4-ylidene)malononitrile,
bis(3-trifluorornethyl-5-(1-isoquinolyl)pyrazolate)(methyldiphenylphosphine) ruthenium,
bis[(4-n-hexylphenyl)isoquinoline](acetylacetonate) iridium(III),
platinum(II) octaethylporphin, bis(2-methyldibenzo[f,h]quinoxaline)(acetylacetonate) iridium(III) and
tris[(4-n-hexylphenyl)isoquinoline] iridium(III).

Specific examples of electron-transporting layer-forming materials include lithium 8-hydroxyquinolinate,
2,2',2"-(1,3,5-benzinetriyl)-tris(1-phenyl-1-H-benzimidazole),
2-(4-biphenyl)-5-(4-tert-butylphenyl)-1,3,4-oxadiazole,
2,9-dimethyl-4,7-diphenyl-1,10-phenanthroline, 4,7-diphenyl-1,10-phenanthroline,
bis(2-methyl-8-quinolinolate)-4-(phenylphenolato)aluminum,
1,3-bis[2-(2,2'-bipyridin-6-yl)-1,3,4-oxadiazo-5-yl]benzene,
6,6'-bis[5-(biphenyl-4-yl)-1,3,4-oxadiazo-2-yl]-2,2'-bipyridine,
3-(4-biphenyl)-4-phenyl-5-tert-butylphenyl-1,2,4-triazole,
4-(naphthalen-1-yl)-3,5-diphenyl-4H-1,2,4-triazole,
2,9-bis(naphthalen-2-yl)-4,7-diphenyl-1,10-phenanthroline,
2,7-bis[2-(2,2'-bipyridin-6-yl)-1,3,4-oxadiazo-5-yl]-9,9-dimethylfluorene,
1,3-bis[2-(4-tert-butylphenyl)-1,3,4-oxadiazo-5-yl]benzene,
tris(2,4,6-trimethyl-3-(pyridin-3-yl)phenyl)borane,
1-methyl-2-(4-(naphthalen-2-yl)phenyl)-1H-imidazo[4,5f][1,10]phenanthroline, 2-(naphthalen-2-yl)-4,7-diphenyl-1,10-phenanthroline, phenyldipyrenylphosphine oxide,
3,3',5,5'-tetra[(m-pyridyl)-phen-3-yl]biphenyl, 1,3,5-tris[(3-pyridyl)-phen-3-yl]benzene,
4,4'-bis(4,6-diphenyl-1,3,5-triazin-2-yl)biphenyl,
1,3-bis[3,5-di(pyridin-3-yl)phenyl]benzene, bis(10-hydroxybenzo[h]quinolinato)beryllium,
diphenylbis(4-(pyridin-3-yl)phenyl)silane and 3,5-di(pyren-1-yl)pyridine.

Examples of electron-injecting layer-forming materials include lithium oxide ($Li_2O$), magnesium oxide (MgO), alumina ($Al_2O_3$), lithium fluoride (LiF), sodium fluoride (NaF), magnesium fluoride ($MgF_2$), cesium fluoride (CsF), strontium fluoride ($SrF_2$), molybdenum trioxide ($MoO_3$), aluminum, lithium acetylacetonate (Li(acac)), lithium acetate and lithium benzoate.

Examples of cathode materials include aluminum, magnesium-silver alloys, aluminum-lithium alloys, lithium, sodium, potassium and cesium.

Another example is described below of a method for producing the organic EL device of the invention in a case where a thin film obtained from the charge-transporting varnish of the invention serves as the hole-injecting layer.

An organic EL device having a charge-transporting thin film formed with the charge-transporting varnish of the invention can be produced by, in the organic EL device production method described above, successively forming a hole-transporting layer and a light-emitting layer instead of carrying out vacuum evaporation operations for a hole-transporting layer, a light-emitting layer, an electron-transporting layer and an electron-injecting layer. Specifically, the charge-transporting varnish of the invention is applied onto an anode substrate, and a hole-injecting layer is formed by the above-described method. A hole-transporting layer and a light-emitting layer are then successively formed thereon, following which a cathode material is vapor-deposited on top, thereby giving an organic EL device.

The cathode and anode materials used here may be similar to those described above, and similar cleaning treatment and surface treatment may be carried out.

The method of forming the hole-transporting layer and the light-emitting layer is exemplified by a film-forming method that involves adding a solvent to a hole-transporting polymer material or a light-emitting polymer material, or to the material obtained by adding a dopant to either of these, thereby dissolving or uniformly dispersing the material, and then applying the solution or dispersion onto the hole-injecting layer or the hole-transporting layer and subsequently baking.

Examples of hole-transporting polymer materials include
poly[(9,9-dihexylfluorenyl-2,7-diyl)-co-(N,N'-bis{p-butylphenyl}-1,4-diaminophenylene)],
poly[(9,9-dioctylfluorenyl-2,7-diyl)-co-(N,N'-bis {p-butylphenyl}-1,1'-biphenylene-4,4-diamine)],
poly[(9,9-bis {1'-penten-5'-yl}fluorenyl-2,7-diyl)-co-(N,N'-bis {p-butylphenyl}-1,4-diaminophenylene)],
poly[N,N'-bis(4-butylphenyl)-N,N'-bis(phenyl)-benzidine] end-capped with polysilsesquioxane and
poly[(9,9-dioctylfluorenyl-2,7-diyl)-co-(4,4'-(N-(p-butylphenyl))diphenylamine)].

Examples of light-emitting polymer materials include polyfluorene derivatives such as poly(9,9-dialkylfluorene) (PDAF), poly(phenylene vinylene) derivatives such as poly (2-methoxy-5-(2'-ethylhexoxy)-1,4-phenylene vinylene) (MEH-PPV), polythiophene derivatives such as poly(3-alkylthiophene) (PAT), and polyvinylcarbazole (PVCz).

Examples of the solvent include toluene, xylene and chloroform. Examples of the method of dissolution or uniform dispersion include stirring, stirring under applied heat, and ultrasonic dispersion.

Examples of the method of application include, but are not particularly limited to, inkjet coating, spraying, dipping, spin coating, transfer printing, roll coating and brush coating. Application is preferably carried out in an inert gas atmosphere such as nitrogen or argon.

Examples of the baking method include methods that involve heating in an oven or on a hot plate, either within an inert gas atmosphere or in a vacuum.

An example is described below of a method for producing the organic EL device of the invention in cases where a thin film obtained from the charge-transporting varnish of the invention serves as a hole-injecting-and-transporting layer.

A hole-injecting-and-transporting layer is formed on an anode substrate. A light-emitting layer, an electron-transporting layer, an electron-injecting layer and a cathode are provided in this order on the hole-injecting-and-transporting layer. Methods of forming the light-emitting layer, electron-transporting layer and electron-injecting layer, and specific examples thereof, include the same as those mentioned above.

The anode material, the light-emitting layer, the light-emitting dopant, the materials which form the electron-transporting layer and the electron-blocking layer, and the cathode material are exemplified in the same way as mentioned above.

A hole-blocking layer, an electron-blocking layer or the like may be optionally provided between the electrodes and any of the above layers. By way of illustration, an example of a material that forms an electron-blocking layer is tris (phenylpyrazole)iridium.

The materials which make up the anode, the cathode and the layers formed therebetween differ according to whether a device provided with a bottom emission structure or a top emission structure is to be fabricated, and so are suitably selected while taking this into account.

Typically, in a device having a bottom emission structure, a transparent anode is used on the substrate side and light is extracted from the substrate side, whereas in a device having a top emission structure, a reflective anode made of metal is used and light is extracted from the transparent electrode (cathode) side in the opposite direction from the substrate. Hence, for example, with regard to the anode material, when fabricating a device having a bottom emission structure, a transparent anode of ITO or the like is used, and when fabricating a device having a top emission structure, a reflective anode of Al/Nd or the like is used.

To prevent deterioration of the device characteristics, the organic EL device of the invention may be sealed in the usual manner with, if necessary, a desiccant or the like.

EXAMPLES

Working Examples and Comparative Examples are given below to more concretely illustrate the invention, although the invention is not limited by these Examples. In the Examples, the following equipment was used for sample preparation and for analyzing physical properties.
(1) $^1$H-NMR Measurement: Ascend 500, from Bruker
(2) Substrate Cleaning: Substrate cleaning machine (reduced-pressure plasma system),
   from Choshu Industry Co., Ltd.
(3) Varnish Coating: MS-A100 Spin Coater,
   from Mikasa Co., Ltd.

(4) Film Thickness Measurement: Surfcorder ET-4000 microfigure measuring instrument, from Kosaka Laboratory, Ltd.

(5) Organic EL Device Fabrication: C-E2L1G1-N Multifunction Vapor Deposition System, from Choshu Industry Co., Ltd.

(6) Measurement of Organic EL Device Brightness:
I-V-L Measurement System
from Tech World, Inc.

[1] Synthesis of Sulfonic Acid Compounds

Comparative Example 1-1

Synthesis of NSO-2

The sulfonic acid compound NSO-2 of the following formula was synthesized in accordance with the method described in WO 2006/025342.

[Chem. 7]

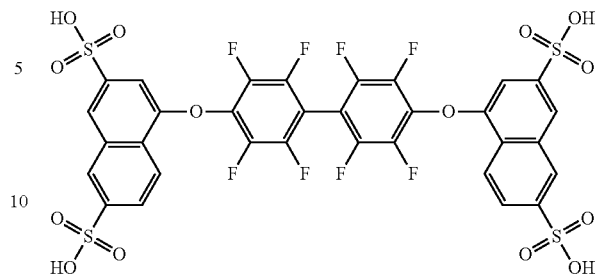

NSO-2

Comparative Example 1-2

Synthesis of NSO-2-PGME

The sulfonic acid ester compound NSO-2-PGME of the following formula was synthesized in accordance with the method described in Patent Document 6.

[Chem. 8]

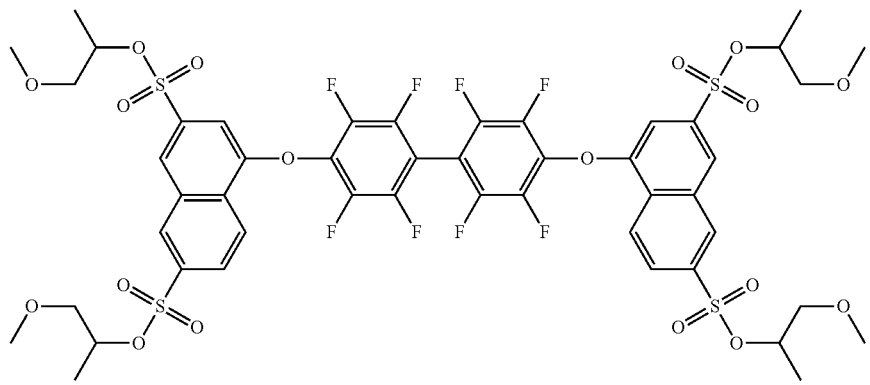

NSO-2-PGME

Working Example 1-1

Synthesis of NSO-2-EH

The sulfonic acid ester compound NSO-2-EH was synthesized in accordance with the following reaction scheme.

[Chem. 9]

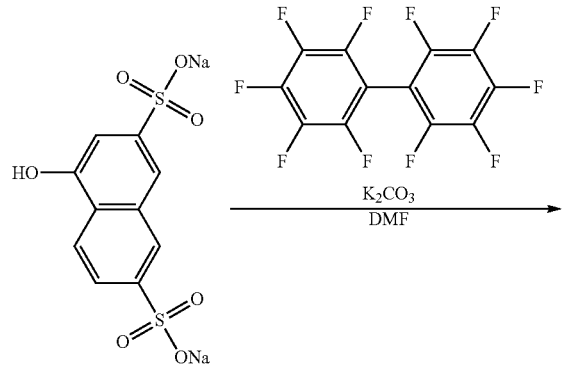

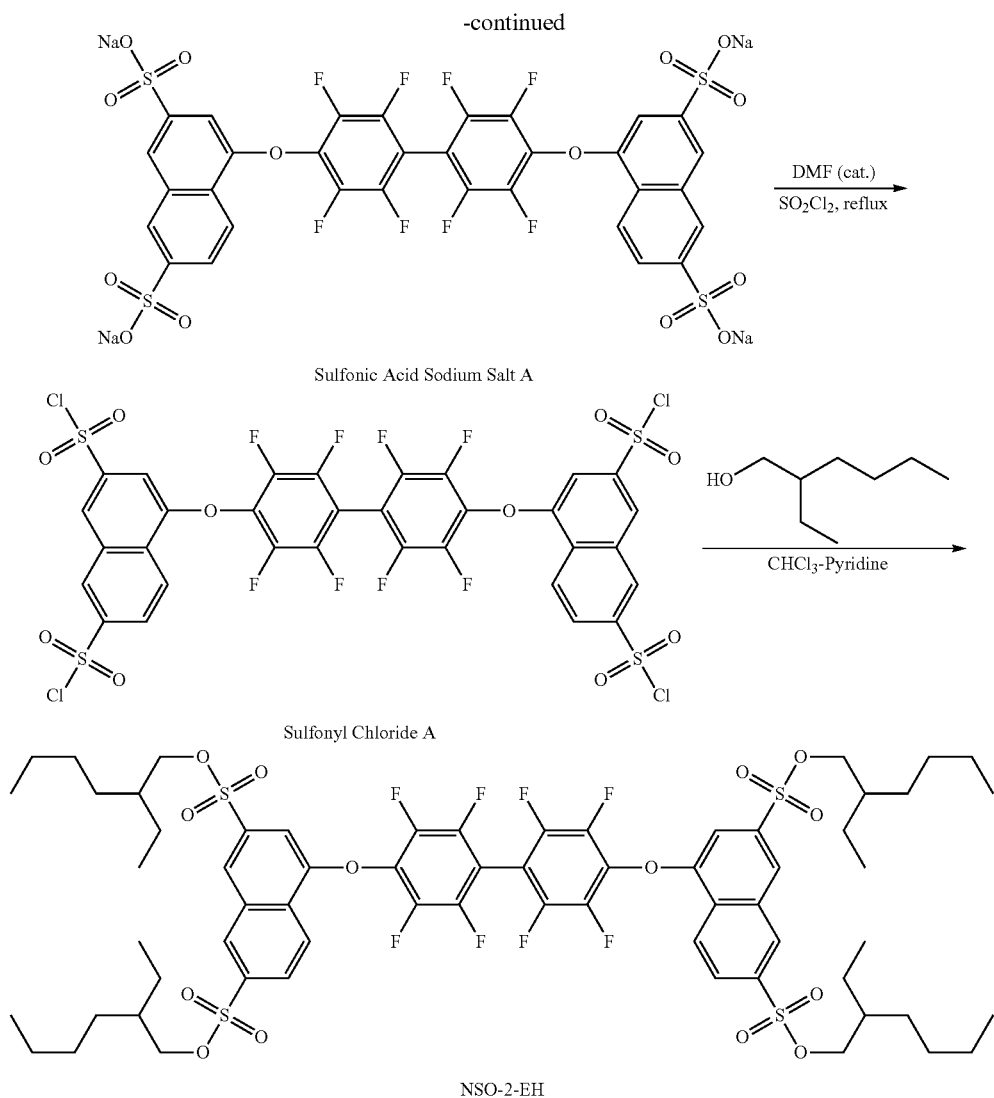

Under a nitrogen atmosphere, 4.8 g (14.36 mol) of perfluorobiphenyl, 4.2 g (30.15 mol) of potassium carbonate and 100 mL of N,N-dimethylformamide were successively added to 11 g (31.59 mmol) of sodium 1-naphthol-3,6-disulfonate, and the reaction system was flushed with nitrogen and subsequently stirred for 6 hours at an internal temperature of 100° C. The system was allowed to cool to room temperature, following which the potassium carbonate residue was removed by filtration and vacuum concentration was carried out. To remove the remaining impurities, 100 mL of methanol was added to the residue and stirring was carried out for 30 minutes at room temperature. The suspension was then filtered, giving 11.8 g (yield, 83%) of Sulfonic Acid Sodium Salt A.

Thionyl chloride (8 mL) and DMF (0.1 mL) were added to 2 g (2 mmol) of Sulfonic Acid Sodium Salt A and the system was refluxed under heating for one hour, following which the thionyl chloride was driven off, giving a solid containing Sulfonyl Chloride A. This compound was used in the next step without further purification.

Chloroform (12 mL) and pyridine (8 mL) were added to this solid, and 3.13 g (24 mmol) of 2-ethyl-1-hexanol was added at 0° C. The temperature was raised to room temperature and 3 hours of stirring was carried out thereafter. The solvent was driven off, following which water was added, extraction was carried out with ethyl acetate, and the organic layer was dried over sodium sulfate. After filtration and concentration, the resulting crude product was purified by silica gel column chromatography (hexane/ethyl acetate), giving 1.25 g of the sulfonic acid ester compound NSO-2-EH as a white solid (yield, 46% (2-step yield from Sulfonic Acid Sodium Salt A). The $^1$H-NMR measurement results are shown below.

$^1$H-NMR (500 MHz, CDCl$_3$) δ:
0.78-0.85 (m, 24H), 1.15-1.39 (m, 32H), 1.58-1.62 (m, 4H), 4.02-4.10 (m, 8H), 7.34 (s, 2H), 8.21 (dd, J=1.5, 9.0 Hz, 2H), 8.44 (s, 2H), 8.67 (d, J=9.0 Hz, 2H), 8.69 (d, J=1.5 Hz, 2H).

Working Example 1-2

Synthesis of NSO-2-BO

Aside from using 4.47 g (24 mmol) of 2-butyl-1-octanol instead of 2-ethyl-1-hexanol, synthesis was carried out in the same way as in Working Example 1-1, giving 1.50 g of the sulfonic acid ester compound NSO-2-BO as a white solid (yield, 48% (two-step yield from Sulfonic Acid Sodium Salt A)). The ¹H-NMR measurement results are shown below.

¹H-NMR (500 MHz, CDCl₃) δ:
0.79-0.87 (m, 2H), 1.17-1.28 (m, 64H), 1.62-1.68 (m, 4H), 4.02 (d, J=5.0 Hz, 4H), 4.08 (d, J=5.0 Hz, 4H), 7.36 (s, 2H), 8.21 (dd, J=1.5, 9.0 Hz, 2H), 8.44 (s, 2H), 8.67 (d, J=9.0 Hz, 2H), 8.69 (d, J=1.5 Hz, 2H).

[2] Production of Charge-Transporting Varnishes and Evaluation of Solubility

Working Example 2-1

Preparation of Charge-Transporting Varnish A

NSO-2-EH (393 mg) and Oligoaniline Compound 1 (133 mg) were added to a mixed solvent of 3-phenoxytoluene (5 g) and tetralin (5 g), and the system was stirred for 5 minutes

[Chem. 10]

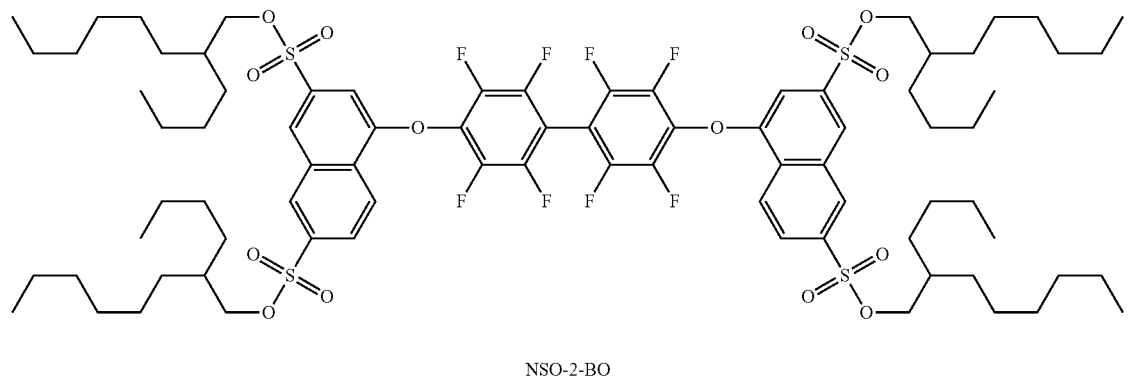

NSO-2-BO

Working Example 1-3

Synthesis of NSO-2-OC

Aside from using 3.13 g (24 mmol) of 1-octanol instead of 2-ethyl-1-hexanol, synthesis was carried out in the same way as in Working Example 1-1, giving 0.13 g of the sulfonic acid ester compound NSO-2-OC as a white solid (yield, 5% (two-step yield from Sulfonic Acid Sodium Salt A)). The ¹H-NMR measurement results are shown below.

¹H-NMR (500 MHz, CDCl₃) δ:
0.82-0.87 (m, 12H), 1.20-1.36 (m, 40H), 1.64-1.74 (m, 8H), 4.11-4.19 (m, 8H), 7.35 (s, 2H), 8.21 (dd, J=2.0, 9.0 Hz, 2H), 8.44 (s, 2H), 8.67 (d, J=9.0 Hz, 2H), 8.68 (d, J=2.0 Hz, 2H).

under heating at 50° C. and 400 rpm. As a result, the NSO-2-EH dissolved completely in the solvent. The resulting solution was filtered using a PTFE filter having a pore size of 0.2 μm, giving Charge-Transporting Varnish A. Oligoaniline Compound 1 was synthesized in accordance with the method described in WO 2013/084664.

[Chem. 12]

Oligoaniline Compound 1

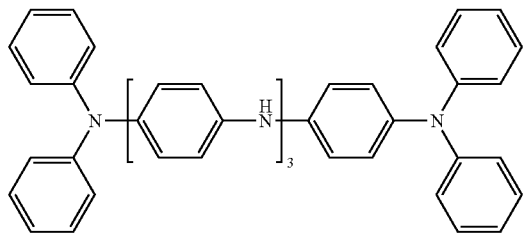

[Chem. 11]

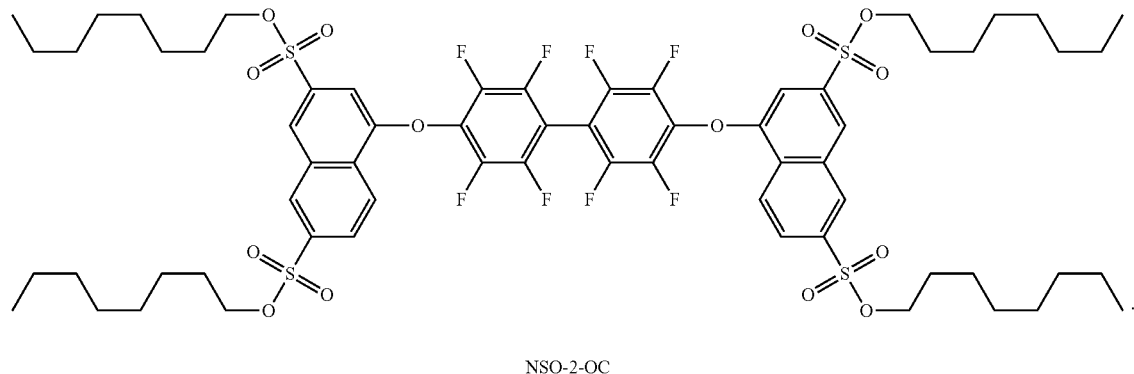

NSO-2-OC

Working Example 2-2

Preparation of Charge-Transporting Varnish B

NSO-2-BO (408 mg) and Oligoaniline Compound 1 (118 mg) were added to a mixed solvent of 3-phenoxytoluene (5 g) and tetralin (5 g), and the system was stirred for 5 minutes under heating at 50° C. and 400 rpm. As a result, the NSO-2-BO dissolved completely in the solvent. The resulting solution was filtered using a PTFE filter having a pore size of 0.2 µm, giving Charge-Transporting Varnish B.

Working Example 2-3

Preparation of Charge-Transporting Varnish C

NSO-2-OC (393 mg) and Oligoaniline Compound 1 (133 mg) were added to a mixed solvent of 3-phenoxytoluene (5 g) and tetralin (5 g), and the system was stirred for 5 minutes under heating at 50° C. and 400 rpm. As a result, the NSO-2-OC dissolved completely in the solvent. The resulting solution was filtered using a PTFE filter having a pore size of 0.2 µm, giving Charge-Transporting Varnish C.

Comparative Example 2-1

Preparation of Charge-Transporting Varnish D

NSO-2-PGME (384 mg) and Oligoaniline Compound 1 (142 mg) were added to a mixed solvent of 3-phenoxytoluene (5 g) and tetralin (5 g), and the system was stirred for 30 minutes under heating at 50° C. and 400 rpm, but some material remained undissolved. With 20 minutes of stirring under heating at 70° C. and 400 rpm, the NSO-2-PGME completely dissolved in the solvent. The resulting solution was filtered using a PTFE filter having a pore size of 0.2 µm, giving Charge-Transporting Varnish D.

Comparative Example 2-2

NSO-2 (349 mg) and Oligoaniline Compound 1 (177 mg) were added to a mixed solvent of 3-phenoxytoluene (5 g) and tetralin (5 g), and the system was stirred for 30 minutes under heating at 90° C. and 400 rpm, but the NSO-2 did not dissolve whatsoever.

Comparative Example 2-3

Preparation of Charge-Transporting Varnish E

NSO-2 (349 mg) and Oligoaniline Compound 1 (177 mg) were added to a mixed solvent of 1,3-dimethyl-2-imidazolidinone (3.3 g), 2,3-butanediol (4 g) and dipropylene glycol monomethyl ether (2.7 g), and the system was stirred for 5 minutes under heating at 50° C. and 400 rpm. As a result, the NSO-2 dissolved completely in the solvent. The resulting solution was filtered using a PTFE filter having a pore size of 0.2 µm, giving Charge-Transporting Varnish E.

NSO-2-EH, NSO-2-BO and NSO-2-OC dissolved completely in a mixed solvent of the low-polarity solvents 3-phenoxytoluene and tetralin when stirred for 5 minutes under heating at 50° C. and 400 rpm, whereas 20 minutes of stirring under heating at 70° C. and 400 rpm was required to completely dissolve NSO-2-PGME in the above mixed solvent, and NSO-2 did not dissolve in this mixed solvent. That is, the sulfonic acid ester compounds of the invention had excellent solubilities in low-polarity solvents.

[3] Evaluation of Shelf Stability of Charge-Transporting Varnish

Working Examples 3-1 to 3-3, Comparative Example 3-1

Charge-Transporting Varnishes A to D were stored under refrigeration at 2° C., and were examined for the presence or absence of precipitate when the periods of time shown in Table 1 below had elapsed following the start of storage. The results are shown in Table 1.

TABLE 1

| | Charge-transporting varnish | Sulfonic acid ester compound | Presence/Absence of precipitate | | | |
|---|---|---|---|---|---|---|
| | | | 6 days | 30 days | 70 days | 350 days |
| Working Example 3-1 | A | NSO-2-EH | no | no | no | no |
| Working Example 3-2 | B | NSO-2-BO | no | no | no | no |
| Working Example 3-3 | C | NSO-2-OC | no | no | no | no |
| Comparative Example 3-1 | D | NSO-2-PGME | yes | — | — | — |

As shown in Table 1, the charge-transporting varnishes that included a sulfonic acid ester compound of the invention had excellent shelf stabilities.

[4] Fabrication of Hole-Only Devices (HOD) and Evaluation of Device Characteristics In the following Working Examples and Comparative Examples, a glass substrate with dimensions of 25 mm×25 mm×0.7 mm (t) and having ITO patterned on the surface to a film thickness of 150 nm was used as the ITO substrate. Prior to use, impurities on the surface were removed with an O₂ plasma cleaning system (150 W, 30 seconds).

Working Example 4-1

Charge-Transporting Varnish A was coated onto the ITO substrate using a spin coater and was subsequently, in open air, pre-baked at 120° C. for 1 minute and then subjected to a main bake at 200° C. for 30 minutes, thereby forming a 30 nm thin film on the ITO substrate.

Using a vapor deposition system (degree of vacuum, $2.0\times10^{-5}$ Pa), thin films of α-NPD and aluminum were successively deposited thereon, giving a hole-only device. Vapor deposition was carried out at a deposition rate of 0.2 nm/s. The thicknesses of the α-NPD thin film and the aluminum thin film were set to respectively 30 nm and 80 nm.

To prevent the device characteristics from deteriorating due to the influence of oxygen, moisture and the like in air, the hole-only device was sealed with sealing substrates, following which the characteristics were evaluated. Sealing was carried out by the following procedure.

The hole-only device was placed between sealing substrates in a nitrogen atmosphere having an oxygen concentration of 2 ppm or less and a dew point of not more than −85° C., and the sealing substrates were laminated together using an adhesive (MORESCO Moisture Cut WB90US(P), from Moresco Corporation). At this time, a desiccant (HD-071010W-40, from Dynic Corporation) was placed, together with the hole-only device, within the sealing substrates. The laminated sealing substrates were irradiated with UV light (wavelength, 365 nm; dosage, 6,000 mJ/cm$^2$) and then annealed at 80° C. for one hour to cure the adhesive.

Working Example 4-2

Aside from using Charge-Transporting Varnish B instead of Charge-Transporting Varnish A, a hole-only device was fabricated in the same way as in Working Example 4-1.

Comparative Example 4-1

Aside from using Charge-Transporting Varnish D instead of Charge-Transporting Varnish A, a hole-only device was fabricated in the same way as in Working Example 4-1.

Comparative Example 4-2

Aside from using Charge-Transporting Varnish E instead of Charge-Transporting Varnish A and carrying out the pre-bake at 80° C. for 1 minute and the main bake at 230° C. for 15 minutes, a hole-only device was fabricated in the same way as in Working Example 4-1.

The current densities at a driving voltage of 3 V were measured for the hole-only devices fabricated in the above Working Examples and Comparative Examples. The results are shown in Table 2.

TABLE 2

| | Charge-transporting varnish | Current density (mA/cm$^2$) |
|---|---|---|
| Working Example 4-1 | A | 1,250 |
| Working Example 4-2 | B | 1,150 |
| Comparative Example 4-1 | D | 771 |
| Comparative Example 4-2 | E | 1,170 |

As shown in Table 2, charge-transporting varnishes containing the sulfonic acid ester compounds of the invention exhibited hole transporting abilities comparable to or better than those of conventional charge-transporting varnishes.

[5] Fabrication of Organic EL Devices and Evaluation of Device Characteristics

In the following Working Examples and Comparative Examples, a glass substrate with dimensions of 25 mm×25 mm×0.7 mm (t) and having ITO patterned on the surface to a film thickness of 150 nm was used as an ITO substrate. Prior to use, impurities on the surface were removed with an O$_2$ plasma cleaning system (150 W, 30 seconds).

Working Example 5-1

Charge-Transporting Varnish A was coated onto the ITO substrate using a spin coater and was subsequently dried at 120° C. for 1 minute and then, in open air, baked at 200° C. for 30 minutes, thereby forming a uniform 30-nm thin film on the ITO substrate.

Next, using a vapor deposition system (degree of vacuum, 1.0×10$^{-5}$ Pa), 30 nm of α-NPD was deposited at a rate of 0.2 nm/s onto the ITO substrate where the thin film was formed, following which CBP and Ir(ppy)$_3$ were co-deposited. Co-deposition was carried out by controlling the rate of deposition such that the concentration of Ir(ppy)$_3$ becomes 6%, to a thickness of 40 nm. Thin films of Alqa, lithium fluoride and aluminum were then successively deposited, thereby giving an organic EL device. At this time, vapor deposition was carried out at a rate of 0.2 nm/s for Alqa and aluminum, and at a rate of 0.02 nm/s for lithium fluoride. The film thicknesses were set to, respectively, 20 nm, 0.5 nm and 80 nm.

To prevent the device characteristics from deteriorating due to the influence of oxygen, moisture and the like in air, the organic EL device was sealed with sealing substrates, following which the characteristics were evaluated. Sealing was carried out in the same way as described above.

Working Example 5-2

Aside from using Charge-Transporting Varnish B instead of Charge-Transporting Varnish A, an organic EL device was fabricated in the same way as in Working Example 4-1.

Comparative Example 5-1

Aside from using Charge-Transporting Varnish D instead of Charge-Transporting Varnish A, an organic EL device was fabricated in the same way as in Working Example 4-1.

Comparative Example 5-2

Aside from using Charge-Transporting Varnish E instead of Charge-Transporting Varnish A and carrying out the pre-bake at 80° C. for 1 minute and the main bake at 230° C. for 15 minutes, an organic EL device was fabricated in the same way as in Working Example 4-1.

The voltages and current efficiencies at a brightness of 1,000 cd/m$^2$ were measured for these devices. The results are shown in Table 3. The size of the light-emitting surface on each device was 2 mm×2 mm.

TABLE 3

| | Charge-transporting varnish | Voltage (V) | Current density (cd/A) |
|---|---|---|---|
| Working Example 5-1 | A | 7.59 | 14.23 |
| Working Example 5-2 | B | 7.58 | 14.70 |
| Comparative Example 5-1 | D | 7.66 | 14.83 |
| Comparative Example 5-2 | E | 7.59 | 14.57 |

As shown in Table 3, charge-transporting varnishes containing sulfonic acid ester compounds of the invention exhibited organic EL characteristics comparable to those of conventional charge-transporting varnishes.

The invention claimed is:

1. A sulfonic acid ester compound of formula (1) below

[Chem. 1]

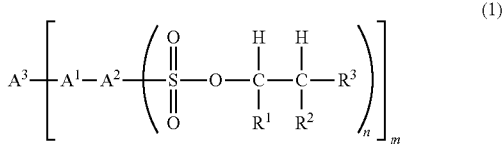

(1)

wherein $R^1$ and $R^2$ are each independently a hydrogen atom or a linear or branched monovalent aliphatic hydrocarbon group, and $R^3$ is a linear or branched monovalent aliphatic hydrocarbon group, the total number of carbon atoms on $R^1$, $R^2$ and $R^3$ being 6 or more;

$A^1$ represents —O— or —S—, $A^2$ is an aromatic group having a valence of n+1, and $A^3$ is a substituted or unsubstituted m-valent hydrocarbon group containing one or more aromatic ring; and m is an integer that satisfies the condition 2≤m≤4, and n is an integer that satisfies the condition 1≤n≤4.

2. The sulfonic acid ester compound of claim 1, wherein $R^1$ is a hydrogen atom, and $R^2$ and $R^3$ are each independently an alkyl group of 1 to 6 carbon atoms.

3. The sulfonic acid ester compound of claim 1 or 2, wherein $A^2$ is a group derived from naphthalene or anthracene.

4. The sulfonic acid ester compound of claim 3, wherein $A^2$ is a group derived from naphthalene.

5. The sulfonic acid ester compound of claim 1, wherein $A^3$ is a group derived from perfluorobiphenyl.

6. The sulfonic acid ester compound of claim 1, wherein m is 2.

7. The sulfonic acid ester compound of claim 1, wherein n is 2.

8. An electron-accepting substance precursor comprising the sulfonic acid ester compound of claim 1.

9. A charge-transporting varnish comprising the electron-accepting substance precursor of claim 8, a charge-transporting substance and an organic solvent.

10. The charge-transporting varnish of claim 9, wherein the organic solvent is a low-polarity organic solvent.

11. The charge-transporting varnish of claim 9 or 10, wherein the charge-transporting substance is an aniline derivative.

12. A charge-transporting thin film produced using the charge-transporting varnish of claim 9.

13. An organic electroluminescent device comprising the charge-transporting thin film of claim 12.

* * * * *